United States Patent [19]
Chelveder et al.

[11] Patent Number: 6,089,078
[45] Date of Patent: Jul. 18, 2000

[54] PROCESS AND DEVICE FOR MEASURING PARTICLES IN SUSPENSION IN A LIQUID

[75] Inventors: Jean-Claude Chelveder, Vitteaux; Fabien Kolly, Martrois; Laurent Morellet, Dijon, all of France

[73] Assignee: Hycel Diagnostics, Pouilly en Auxois, France

[21] Appl. No.: 09/129,453

[22] Filed: Aug. 6, 1998

[30] Foreign Application Priority Data

Apr. 8, 1998 [FR] France .................................. 98 04395

[51] Int. Cl.⁷ .......................... G01N 21/84; G01N 15/02; G06F 19/00
[52] U.S. Cl. .......................... 73/61.71; 73/61.73; 356/73; 356/335; 356/442; 324/71.4; 324/701
[58] Field of Search ............................... 73/61.71, 61.73, 73/23.24, 24.03, 28.01; 324/693, 701, 71.4; 356/39, 335, 442, 73

[56] References Cited

U.S. PATENT DOCUMENTS

| | | | |
|---|---|---|---|
| 3,864,571 | 2/1975 | Stillman et al. | 250/302 |
| 4,003,707 | 1/1977 | Lübbers et al. | 23/232 R |
| 4,683,212 | 7/1987 | Uffenheimer | 436/52 |
| 5,106,187 | 4/1992 | Bezanson | 356/73 |
| 5,182,617 | 1/1993 | Yaneyama et al. | 356/440 |
| 5,235,844 | 8/1993 | Bonne et al. | 73/24.01 |
| 5,343,760 | 9/1994 | Sultan et al. | 73/861.04 |
| 5,408,307 | 4/1995 | Yamamoto et al. | 256/73 |
| 5,465,608 | 11/1995 | Lokshin et al. | 73/24.01 |
| 5,488,469 | 1/1996 | Yamamoto et al. | 356/39 |
| 5,488,649 | 1/1996 | Yamamoto et al. | 356/724 |
| 5,524,477 | 6/1996 | Wajid | 73/24.05 |
| 5,542,298 | 8/1996 | Sarvazian et al. | 73/597 |
| 5,543,113 | 8/1996 | Koike et al. | 422/83 |
| 5,604,335 | 2/1997 | Isahaya | 177/210 FP |
| 5,623,200 | 4/1997 | Ogino | 324/71.4 |
| 5,709,792 | 1/1998 | Zdanevitch et al. | 205/775 |
| 5,780,724 | 7/1998 | Oleander et al. | 73/40.5 A |
| 5,831,145 | 11/1998 | Logothetis et al. | 73/23.2 |
| 5,900,533 | 5/1999 | Chou | 73/24.01 |

FOREIGN PATENT DOCUMENTS

| | | | |
|---|---|---|---|
| 0 679 889 A2 | 4/1995 | European Pat. Off. | G01N 33/483 |
| 2 733 596 | 10/1996 | France | G01N 33/48 |

*Primary Examiner*—Hezron Williams
*Assistant Examiner*—J. David Wiggins
*Attorney, Agent, or Firm*—Jacobson, Price, Holman & Stern, PLLC

[57] ABSTRACT

A process provides for measuring particles in suspension in a liquid in an particle response analyzing instrument comprising a cytometric flow cell head, wherein the suspension is injected into the head at an injection rate, the head comprises one or several sensors which deliver responses when measuring particles injected therein and which yield a significant response for a set measurement frequency range. The response is processed and used to generate results in the instrument. When a first response is significant, measurements continue at the same injection rate in order to obtain a result thats likely to continue being a significant response during subsequent measurements and, conversely, when the first response is not significant, the injection rate is modified in order to bring the response within a significant response range and to continue with measurements in order to obtain a result.

13 Claims, 2 Drawing Sheets

PROCESS AND DEVICE FOR MEASURING PARTICLES IN SUSPENSION IN A LIQUID

FIELD OF THE INVENTION

This invention relates to a process and a measuring device for articles in suspension in a liquid. It finds especially applications in haematology, to characterize blood cells and provide results on parameters that we want to measure on the basis of blood samples.

Analyses conducted in haematology aim at identifying and counting several categories of cells, in order to obtain diagnostics. The cells to be recognized are usually red corpuscles, thrombocytes and white corpuscles, the latter being distributed into several families, such as lymphocytes, monocytes or granulocytes.

Counting measurements are conventionally performed in haematology by impedancemetry (or Coulter effect). To do so, diluted blood samples, containing cells in a conducting liquid, are injected through a small-diameter orifice, at which electric current is applied and maintained at constant level. The passage of a particle then causes a transitory resistivity variation, representative of the volume occupied by the passing cell. This impedance variation measuring process makes it possible to distinguish the cells in relation to their volumes.

Other measurements implement optical means. Such light beam measurements enable distinctions differing from those obtained by impedancemetry. Measurements carried out using both these means are sometimes conducted correlatively.

A device allowing to conduct this type of measurement on blood samples and comprising this type of sensors will be called cytometric head, at a later stage.

Such devices are not limited to haematology applications, but can also be used to measure characteristics of all types of particles in suspension in a liquid. In particular, calibration of this type of device can be performed with non-biological particles in suspension in a liquid.

Whatever the type of sensor and the signal conditioning and processing chain used, particles to be characterized pass through it at a given speed. Each passage of a particle causes the appearance of a signal or response which increases, reaches a peak value, then decreases. This response, called event, is usually characterized by the peak value or by a time-related integration of the signal. The word sensor will be used to designate the sensor assembly and its signal conditioning and processing chain, whereas such a chain may comprise filters, integrators or any other electronic device acting upon the signal.

In the case of a diluted blood sample, injected into the cytometric head, the sample is passed through one or several sensors. A set of blood cells thus generates events in each of the sensors used. Characteristic values of the events are measured and distributed along ranges of juxtaposed values called channels.

Such a device has already been described in the patent FR-2 733 596 for <<a process and device for identification of particles>>.

The sensors are not perfect and must operate within a zone corresponding to their optimum or significant operating range or optimum or significant response zone. For a sensor whose response curve is substantially linear, this optimum zone can be centered around the linear range. For a sensor whose response curve is substantially sigmoid, the optimum or significant zone can be centered around the inflection point of the response curve. If the sensors are not within their optimum or significant operating range, the exploitation of the measurement is not so efficient.

In the case of a device comprising a cytometric head, the dilution of the sample and its injection rate into the cytometric head are selected so that for a given device and for samples according to the standards, the sensors are, each, within their optimum or significant response zones. These conditions are obtained statistically from samples derived from a representative population. In the case of haematology analyses, there are, for example, standards for the number of corpuscles per volume unit (this number is here representative of the dilution), for the proportion in % or for the absolute value in number per volume unit of the various types of corpuscles. The dilution and injection rates are therefore standard for the device considered.

Consequently, if a sample exceeds the limits, the sensors may also shoot out of their optimum or significant response zones. For instance, if energized too frequently, a sensor may miss out measurements for example because the time-related definition of the sensor is limited. Usually, statistic processing enables to correct the so-called coincidence phenomenon. Such a method also finds its limits. Classically, the concentration in white corpuscles can only be measured up to about 100,000 cells per $mm^3$. Beyond these values, the sensor shoots out of its significant response range and it has today become a requirement to repeat the analysis after manual predilution of the sample.

This solution has a number of shortcomings. In all cases, time is wasted since the initial measurements are rejected and additional handling of the sample, lengthy and liable to cause errors, proves necessary. This additional handling can become a source of accidents and of contamination of the staff by biological and/or chemical products. The tubes containing the blood samples are closed by plugs which must be opened . . . The costs are increased by the use of specialized staff who must be provided in case when handling operations should become necessary. Additional consumables must also be employed.

BACKGROUND OF THE INVENTION

The aim of the present invention is to remedy these shortcomings, thanks to a process and a device which make it possible to widen considerably the optimum or significant measuring range.

The purpose of the invention is therefore to reduce noticeably the costs, the duration and the risks related to blood examination, without detriment to the reliability of the results.

SUMMARY OF THE INVENTION

The invention relates to a process and a device for measuring articles in suspension in a liquid in an instrument comprising a cytometric head, whereby the said suspension is injected into the said head with an injection rate thanks to the action of a pump, whereas the said head comprises one or several sensors delivering responses when measuring particles and having a significant response for a set measurement frequency range, whereas the responses are processed and used to generate results in the said instrument. According to the invention:

- if the first responses are significant, the measurements continue with the same injection rate in order to obtain a result,
- conversely, if the first responses are not significant, the injection rate is modified in order to bring the responses back within the significant response range and to continue with the measurements in order to obtain a result.

According to various embodiments of the invention, each exhibiting particular advantages, the following steps and means can be used, with various technically possible combinations:

whereby the process can be broken down into:

step 1: a measurement E of the sensor response for the initial injection rate d of the suspension is carried out, step 2: comparison of the measurement E with two limits P1 and P2 delineating a significant response range of the sensor with $P1 \leq P2$, step 3: if $P1<E<P2$, the injection rate of the sample does not change, step 3': if $E<P1$ or $E>P2$, the injection rate of the suspension is changed, whereas the injection rate correction coefficient k is calculated so that the sensor operates within its significant response range, with this new injection rate $d'=d/k$.

the measurement E of the sensor response is taken by counting a number n of particles within a certain duration, using the sensor, and k is calculated by $k*n1<n<k*n2$ with n1 and n2 delineating the limits of a significant response range of the said sensor in number of particles counted over the said duration.

the measurement E of the sensor response is conducted on the basis of a number Ne of unit measurements, whereas a unit measurement corresponds to the set of responses processed within a time unit.

on the basis of the global measurement constituted of the number Nt of unit measurements made on the suspension, a number Nu of the said unit measurements enables to obtain the useful measurement which will serve to deliver the result for the parameter with $Nu \leq Nt$.

the measuring device comprises means to process the responses from the sensors and means to control the pump in relation to the responses delivered by the sensors.

the pump is a syringe carrier system.

the measuring head comprises at least one impedancemetric sensor.

the measuring head comprises at least one optical sensor.

the suspension injected is a diluted blood sample.

Thanks to the present invention, considerable time is gained with respect to the previous solutions. It is not necessary any longer to modify the dilution of the suspension nor to have it pass through the measuring head a second time.

The risks associated with the handling of the blood and of the biological samples in the case of a biological measuring instrument do not exist any more. Saving on consumables also constitutes a financial advantage.

The present invention will be understood better when reading the following description of an embodiment of the process according to the invention and of a device according to the invention given for exemplification purposes and not limiting in any respect, with reference to the appended drawings. This mode corresponds to the measurement of biological suspensions and more particularly the use of blood samples diluted in a cytometric head.

DETAILED DESCRIPTION OF THE PREFERRED EMBODIMENT

Figure 1:
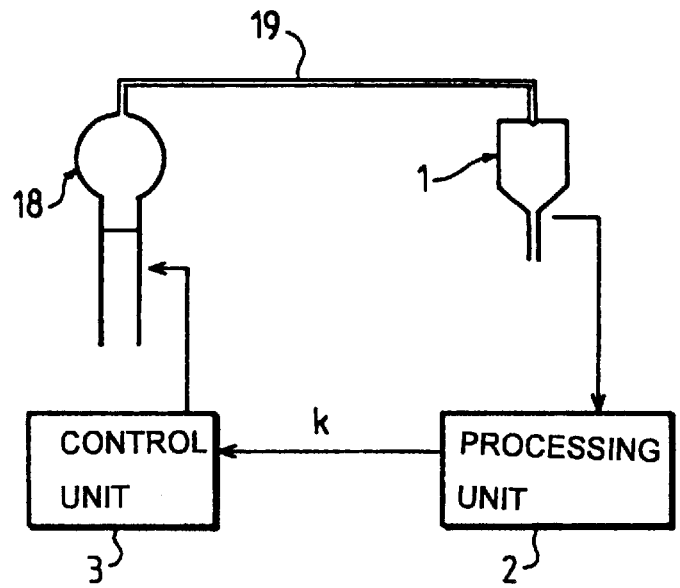
FIG. 1 is a sketch of a device with a cytometric head according to the invention.

A device with a cytometric head according to the invention, represented on FIG. 1, comprises a cytometric head 1 designed for conducting measurements on samples comprising biological cells. It also comprises a unit for processing the responses 2 connected to the cytometric head 1 and receiving at input the responses from the sensors of the cytometric head. The processing unit 2 which comprises electronic computing means delivers the information k to the control unit 3.

The control unit 3 operates the pumping device which is on FIG. 1, a syringe carrier 18 designed for injecting the samples into the cytometric head through a fluid system 19.

Physically, the signal processing unit and the control unit can be separate or combined. They consist of conventional electronic elements, enabling to perform analogue and digital operations. Especially, the processing unit enables to calculate the correction coefficient k which is sent to the control unit.

Figure 2:
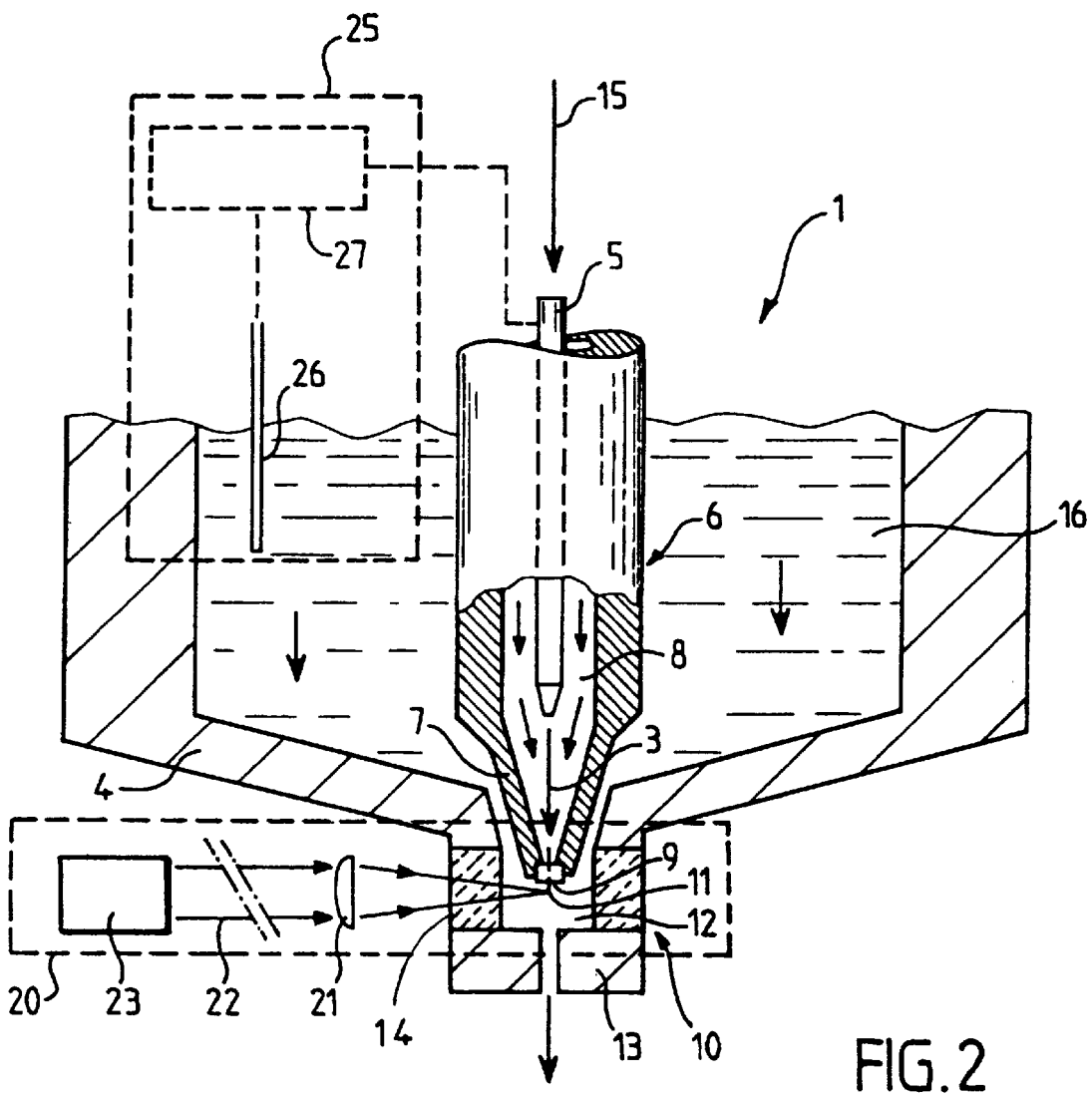
FIG. 2 is a schematical view of a cytometric head used in the device of FIG. 1.

The cytometric head 1, detailed on FIG. 2, comprises a casing 4 with a spindle 15 containing an injector 5 allowing the passage of biological cells in suspension, which are more precisely, in the example under consideration, blood cells. The injector 5 is included in a flow chamber 6 inside the casing 4, which contains a driving liquid 8 and which is terminated by a nozzle 7. The injector 5 and the flow chamber 6 are oriented following the spindle 15 and enable to obtain an axial flow, whereas the cell suspension is guided over its trajectory by the driving liquid. The nozzle 7 concentrates the flow in the direction 15. It is terminated at its extremity 9 by a very small orifice, typically of a fraction of a millimeter in diameter and enabling to measure the electric impedance.

The cytometric head 1 also comprises an optical sensor 20. The latter contains an optical device 10. An optical element 14 comprises internally a chamber 12, open in two opposed extremities with respect to the spindle 15 and centered around a point 11. The optical element 14 is fastened to the casing 4 so that the nozzle 7 ends in the chamber 12 through one extremity of the latter and so that the flow of cells goes through the center point 11 of the chamber 12. An outlet device 13 is fastened to the optical element 14. The cell flow comes out of the chamber 12 through the outlet device 13.

The optical sensor 20 also comprises a laser diode 23 capable of emitting a light beam 22 focused on the cell flow, at the center point 11 of the chamber 12 in which it enters via the optical element 14. The optical sensor 20 also comprises a sensing set (not represented), which measures the light diffused by the cells.

The volume delineated by the casing 4 and the chamber 12 is filled with an electrically conducting liquid 16. This liquid 16 washes permanently the optical device 10 and prevents cell recirculations in front of the beam light 22.

The cytometric head 1 also comprises an impedance sensor 25, consisting of electronic measuring means 27 connected to the injector 5 forming a first electrode and a second electrode 26. The electrode 26 is arranged in the volume delineated by the casing 4, filled with the electrically conducting liquid 16. The electronic means 27 and the electrode 26 enable to count electronically the number of cells through the orifice 9 and to measure the volume electrically, according to an impedancemetric method (said Coulter-method).

During operation, a suspension of biological cells is injected in the injector 5. Having reached the extremity of the injector 5, the cell flow is driven and guided by the driving liquid 8 to the extremity 9 of the nozzle 7. They go then through the chamber 12 and are finally evacuated through the outlet device 13.

The number of cells in the measurements must be sufficiently high to be representative. For instance, this number is set at least to 10,000, whereas the analysis duration ranges between 5 and 20 seconds.

Figure 3:
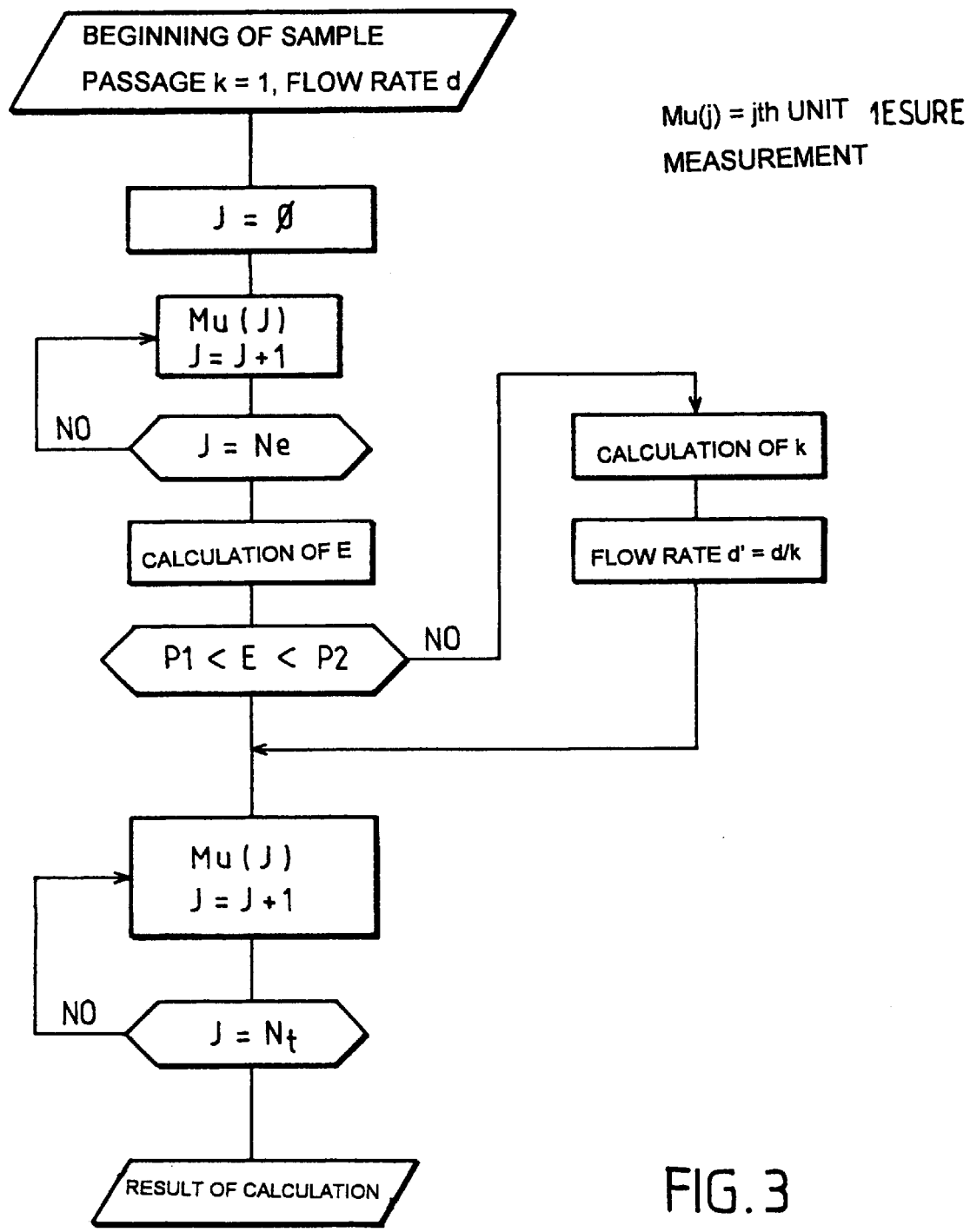
FIG. 3 represents a flow chart for the implementation of the process according to an embodiment of the invention.

An embodiment of the process with the corresponding flow chart, FIG. 3, is described below. In such a case, the sensors operate as counting devices and are considered as having a linear response curve. A unit measurement corresponds to the set of signals processed in a time unit. These processed signals correspond to the cells of the sample which have been detected by the sensors. By global measurement, we mean the total number Nt of the unit measurements corresponding to a sample, Nt can be for instance equal to 40. The duration of a unit measurement being for example of 250 ms, the total duration of the measurements for a sample is then 10 s. The result delivered by the machine comes from the useful measurement, consisting of Nu unit measurements, in this mode Nu≦Nt.

On FIG. 3, j is a counting variable of the unit measurements, which is reset at the beginning of the passage of the sample. Mu (j) corresponds to the Jth unit measurement.

At the beginning of the passage of the cellular suspension in the cytometric head at the initial injection rate v, a certain number Ne of unit measurements are performed and used to calculate the number of cells counted during a time unit, i.e. E the result of this calculation, Ne can, for example, be equal to 4.

A test is performed, consisting in comparing E with two limits P1 and P2 of a significant response range of the sensor. These limits correspond to values for which the sensors operate within their significant response ranges and correlation will only take place if E is outside this response range.

If E ranges between the limits P1 and P2, no correction of the injection rate is performed. The unit measurements remaining to be conducted on the sample will be taken with the initial injection rate d. In such a case, we have Nu=Nt, the result is derived from the set of the unit measurements performed on the sample.

If E is outside the value range delineated by P1 and P2, the injection rate d of the sample in the cytometric head is modified in d'. A correction factor k of the flow is predetermined or calculated: d'=d/k.

The value of k can also be determined by a slaving process with an iterative loop in order to bring E back between P1 and P2.

In the cytometric head, the diameter of the cell flow and, hence, the number of cells per length unit of the flow, depends for a given dilution, on the injection rate imposed by the pump, on the diameter of the orifice and on the differential pressure on both sides of this orifice.

The speed at which the cells pass through the orifice depends on the differential pressure on both sides of this orifice.

Thus, for instance, acting on the differential pressure enables to control the speed of passage of the cells going through the device.

For a given differential pressure, a given orifice diameter, a given dilution rate, the passage frequency of the cells in the device can be adjusted while acting on the injection rate of the suspension of particles imposed by the pump (or syringe carrier).

The injection rate is adjusted and the measurements resume at the injection rate d'. In this mode, the number Nt of unit measurements performed on each sample is the same for all the samples. If the flow is modified, Nu=Nt−Ne unit measurements are used to provide the result.

k can have the following values:

k<1, then the injection rate of the sample is increased: d'>d, k=1, the injection rate remains constant, k>1, the injection rate is decreased: d'<d.

Limits could be set for the value of the correction coefficient k. These limits will depend on factors such as the response curve of the sensor or on external factors such as the performances of the pumping device, the characteristics of the cytometric head (maximum working pressure), the fluids used (viscosity), etc.

The limits P1, P2 for the sensor are conventionally stored in electronic memories. They can then be modified in relation to the result of the calibration operations performed on the machine.

The device for the implementation of the process of the invention according to an embodiment, comprises the following means which are elements of an instrument designed for delivering results on the basis of measurements on diluted blood sample cells.

A cytometric head comprising one or several sensors capable to supply signals, whereas the said sensors are impedancemetric and/or optical.

signal processing means. These are conventional analogue and digital electronic means. In particular, electronic computing means whose memories can store the different elements necessary to the tests and calculations of k.

a pump, preferably, a device such as syringe carrier, injecting the blood samples into the cytometric head. The said pump is operated by conventional electronic control means.

a fluid system between the pump and the cytometric head.

a link between the signal processing means and the control means of the pump ensures exploitation of the correction coefficient k of the rate.

The control and processing means can physically consist of electronic modules, separated or conversely, combined.

Any device and instrument enabling implementation of the process of the invention and which could be contemplated as obvious by the man skilled in the art, are part of this description. Moreover, the detailed description and the examples provided are simply illustrative and indicative and do not limit the scope of the invention.

What is claimed is:

1. A process for measuring samples of particles in suspension in a liquid in a particle response analyzing instrument comprising a cytometric flow cell head with a flow restriction or sensing zone for determining any changes in physical, optical or electrical properties of said liquid as said particles therein pass through said flow restriction or sensing zone, whereby the said suspension is injected by a pump into the head at an injection rate d that characterizes a variable measurement frequency, said head comprising a sensor, said particles being injected one at a time into the sensor, said sensor delivering a response when one particle is in said sensor, said response being significant when the frequency of measurements for the injected particle is comprised in a defined measurement frequency range known to correspond with optimum output response range, whereas responses for a sample comprise first responses and further responses and whereas results for a sample are generated by processing significant responses in said instrument, wherein if the first responses are significant, the measurements continue with the same injection rate d to get further responses, and conversely, if instead the first responses are not significant, the injection rate is modified to either plus or minus d'=d/k, where k is the injection rate direction coefficient, in order to obtain significant further responses by modifying said variable measurement frequency back within said defined measurement frequency range.

2. A measuring process according to claim 1, whereas the sensor has a significant response range corresponding to said defined frequency range of measurement, said significant response range being delineated by two limits P1 and P2 with P1≦P2, comprising the following steps:

step 1: a measurement E of the sensor response for the injection rate d of the suspension is carried out, step 2: comparison of the measurement E with said significant response range, step 3: if P1<E<P2, the injection rate d does not change, step 3': if E<P1 or E>P2, the injection rate is changed to d'=d/k.

3. A process according to claim 2, where a measurement E of the sensor response is a count of a number n of particles within a certain duration and the two limits of the significant response range are n1 and n2 expressed as a number of particles over said duration, wherein k is obtained by the resolution of k*n1<n<k*n2.

4. A process according to claim 3, wherein a unit measurement is a set of responses processed within a time unit duration and a number Nt of unit measurements are taken for each sample, wherein the measurement E of the sensor response is conducted on the basis of a number Ne of unit measurements and the result is processed from a number Nu of unit measurements with Nu≦Nt.

5. A process according to claim 1, wherein the suspension injected is a diluted blood sample.

6. A particle response measuring device for analyzing particles suspended in a liquid comprising a cytometric flow cell measuring head with a flow restriction or sensing zone for determining any changes in a physical, optical or electrical properties of said liquid as said particles therein pass thru said flow restriction or sensing zone, a sensor for delivering an initial output response when a particle is injected therein, pump means to inject the liquid suspension of particles at a variable injection rate that characterizes a variable measurement frequency into the measuring head and, one particle at a time, into the sensor, means for processing the initial response, said response of sensor output being sufficient when said variable frequency of measurements for the injected particles is within a defined measurement frequency range known to correspond with optimum sensor output response range, and means to modify the variable injection rate to obtain a significant response when an initial response is not significant.

7. A measuring device according to claim 6 wherein the sensor is at least one impedancemetric sensor.

8. A measuring device according to claim 6 wherein the pump is a syringe carrier system.

9. A measuring device according to claim 8 wherein the sensor is at least one impedancemetric sensor.

10. A measuring device according to claim 6 wherein the sensor is at least one optical sensor.

11. A measuring device according to claim 8 wherein the sensor is at least one optical sensor.

12. A measuring device according to claim 6 which further comprises means to control the pump means in relationship to responses delivered by the sensor.

13. A measuring device according to claim 6 with double hydrodynamic focusing comprising both a driving liquid and a cell-recirculation-preventing liquid.

* * * * *